United States Patent [19]

Gregory

[11] Patent Number: 4,493,039

[45] Date of Patent: Jan. 8, 1985

[54] APPARATUS AND METHOD FOR IMAGE REPRODUCTION OF MATERIALS USING THEIR MAGNETIC AND ELECTRIC PROPERTIES

[75] Inventor: William D. Gregory, NE. Vienna, Va.

[73] Assignee: President and Directors of Georgetown University, Washington, D.C.

[21] Appl. No.: 147,297

[22] Filed: May 6, 1980

[51] Int. Cl.³ .............................................. G06F 15/42
[52] U.S. Cl. ................................ 364/414; 324/61 R; 324/233; 324/228
[58] Field of Search .................... 364/413–415, 364/516–517; 324/61 R, 200, 228, 232, 233, 262, 239; 128/653

[56] References Cited

U.S. PATENT DOCUMENTS

| | | | |
|---|---|---|---|
| 3,619,771 | 11/1971 | Hentschel | 324/239 |
| 3,922,552 | 11/1975 | Ledley | 250/445 T |
| 3,934,142 | 1/1976 | Hounsfield | 250/445 T |
| 3,936,636 | 2/1976 | Percival | 250/336 |
| 3,973,127 | 8/1976 | Matsuda et al. | 250/445 T |
| 4,079,730 | 3/1978 | Wikswo, Jr. et al. | 128/653 |
| 4,134,395 | 1/1979 | Davis | 128/653 |
| 4,135,247 | 1/1979 | Gordon et al. | 364/414 |
| 4,136,388 | 1/1979 | Lindquist | 364/414 |
| 4,138,721 | 2/1979 | Boyd | 364/414 |
| 4,144,877 | 3/1979 | Frei et al. | 128/25 |
| 4,250,451 | 2/1981 | Slagle | 324/262 |
| 4,263,551 | 4/1981 | Gregory et al. | 324/233 |

FOREIGN PATENT DOCUMENTS 1240194 7/1971 United Kingdom ................ 324/200

OTHER PUBLICATIONS

"Proton Spin Imaging by Nuclear Magnetic Resonance", Mansfield, Journal of Contemporary Physics, vol. 17, No. 6, 553–576, 1976.

"Complex Bioelectric Impedance Measurements for the Detection of Pulmonary Edema", Ackman et al., Digest of the 11th International Conference on Medical and Biological Engineering, 288–289, 1976.

"Abnormal Electrical Properties Betray Breast Tumors to Scanner", Electronics International, 70–71, Jan. 3, 1980.

"Measurement Errors and Origin of Electrical Impedence Changes in the Limb", Swanson, Masters Thesis, 181–203, 1976.

"Image Reconstruction From Projections", Gordon et al., Scientific American, 56, Oct., 1975.

"Reconstruction of the Three–Dimensional Refractive Index Field From Multi–Directional Interferometric Data", Sweeney et al., Applied Optics, 2649–2664, Nov. 1973.

"In Impedance Camera for Spacially Specific Measurements of the Thorax", Henderson et al., IEEE Transaction On Biomedical Engineering, 250–254, May 1978.

"New Views Into Body Aid Diagnosis", B. Rensberger, N.Y. Times, C1, Nov. 14, 1978.

Primary Examiner—Errol A. Krass
Assistant Examiner—Gary Chin
Attorney, Agent, or Firm—Oblon, Fisher, Spivak, McClelland & Maier

[57] ABSTRACT

Pictorial images of selected volume elements of materials are generated by a contactless, non-destructive, substantially hazard free tomographic technique in which the material is brought within the influence of a relatively low-strength electromagnetic field and subjected to plural preselected frequencies to provide output data which is used to generate an image reflective of the magnetic and/or electric and/or conductance properties of the selected volume elements. This data has a high volume information content which enables accurate and reproducible identification of the material under investigation. The technique has application in the medical diagnostic field such as for example in aiding in the detection of small areas of cancerous tissue present in a larger mass of healthy tissue.

17 Claims, 18 Drawing Figures

(List continued on next page.)

OTHER PUBLICATIONS

"Two-Dimensional Aerial Smoothing in Radio Astronomy", R. N. Bracewell, Australian Journal of Physics, 297–314, 1956.

"Computerized Tomography: Taking Sectional X-Rays", Swindell et al., Physics Today, 32–41, 1977.

"Two-Dimensional Analysis of Electrical Fields in the Human Body", Guha et al., I.E. Journal IDGE, 4–7, 1972.

"Computer-Aided Ultrasonic Diagnosis Equipment for Simultaneous Tomograph Method", Yokoi et al., Toshida Review, Aug. 1973.

"Development of Computer Systems for Radiotherapy of Cancer", Umegaki, Japan Clinical Oncology, vol. 1, No. 1, Jan. 1971.

"Dynamic Display of Radiotherapy Plans Using Computer-Produced Films", Sterling et al., Work in Progress, Jun. 1973.

"Electrical Impedance Computer Tomography (ICT): A New CT Imaging Technique", Price, West Coast Symposium, Jan. 17–19, 1979.

"The Siretom, A Computerized Transverse Axial Tomograph for Brain Scanning", K. Fuhrer et al., Electromedica, 2–3, 1975.

"An Integrated Ultrasound-Computer Dosimetry System for Radiation Therapy", J. M. Slater et al., Proceedings of the Symposium on Advance in Biomedical Dosimetry, Vienna, Austria, 10–14, Mar. 1975.

"Computing Techniques Allow Whole-Body X-Ray Pictures in Minutes", p. 50 from Developments.

BEFORE ITERATION

AFTER ITERATION

APPARATUS AND METHOD FOR IMAGE REPRODUCTION OF MATERIALS USING THEIR MAGNETIC AND ELECTRIC PROPERTIES

The present invention relates to an apparatus and method for generating pictorial images of a material under investigation using its magnetic and/or electric permeability and/or conductance properties at various applied frequencies.

BACKGROUND OF THE INVENTION

In recent years, several new non-destructive analytical techniques have been developed for investigating the internal properties of materials. By utilizing a technique which has been variously referred to as "computer tomography", "computerized axial tomography", "transaxial tomography" and "reconstruction from projections", it is possible to generate a picture of an object along a thin cross-sectional slice of the body. At present, there are five general areas which utilize tomographic techniques for generating cross-sectional pictures of objects, and these are transmission tomography, emission tomography, ultrasound tomography, electrical impedance tomography, and nuclear magnetic resonance tomography. Each of these areas will be summarized below.

Much of the early work in the field of image construction utilizing tomographic techniques centered on the use of X-rays and other narrow beam penetrating radiation, for example gamma rays. These transmission techniques have found major application in the medical diagnostic field although other analytical applications have been described. In the X-ray tomography technique, a two dimensional cross-sectional image is reconstructed by taking a large number of transmission measurements through the slice of interest using an X-ray source-detector assembly. The assembly is rotated uniformly about the body as the measurements are taken, and by restricting the measurements to parts of the body contained only in the slice of interest, information from other parts of the body is automatically excluded from the data. The measurements are usually carried out at a single frequency, and the quantity measured and displayed is the X-ray absorption at each volume element (or pixel) within the slice of interest. In the normal arrangement for medical application, the patient remains stationary and the X-ray source-detector assembly is translated and rotated around the patient. However, in other possible applications, the object may be moved relative to the X-ray source-detector assembly. In more recent machines, the X-rays are formed into a fan of pencil beams which encompasses the section of interest so that movement of the X-ray source-detector assembly and the object relative to each other is significantly reduced. Although modern X-ray tomography machines are extremely fast in the data collection process, typically taking between five and ten seconds for the whole operation, there is nevertheless the acknowledged radiation health hazard due to the presence of X-rays. In addition, X-ray tomography equipment is extremely costly from both the manufacturing and operation/maintainence standpoints. In view of this, research into the development of lower cost X-ray tomography equipment with improved radiation shielding and lower exposure times is currently underway, but the radiation hazard to the patient does nevertheless detract from the use of this technique.

Emission tomography differs somewhat from transmission tomography in that, instead of beaming penetrating radiation through a selected slice of the body and measuring the amount coming out of the other side, as in X-ray tomography, penetrating radiation emitted from special radioactive chemicals taken into the body is measured and used to generate an image of the area through which the emission beam passes. Like X-ray tomography, emission tomography suffers from the same health hazard problem arising from the radioactive emissions. Further disadvantages arise from the fact that the radioactive organic compounds first must be synthesized, usually requiring the use of a cyclotron which is an extremely expensive process, and then the compounds, when so formed, must be used almost immediately because of their relatively short halflife.

In the ultrasound tomography technique, high-frequency ultrasonic pulses are transmitted into the body and, using tomographic techniques, pictures of the shape of tissues are reconstructed from reflected pulses (echo data). As the traveling ultrasonic pulses encounter changes in densities in the body, part of the pulse is reflected back to a detector which is usually pressed against the body. The other part of the pulse not encountering a change in density travels on through the body. Thus, ultrasound tomography differs from transmission and emission tomography in that it is a pulse reflection technique, and in most instances requires the detector to be in physical contact with the body under investigation. An advantage of the use of high-frequency ultrasonic pulses is that there is no known health hazard to the patient. However, this technique suffers from several disadvantages, the main ones being that the echo data often contains considerable noise, and the pulse detector must be in good skin contact on the surface of the body to ensure that the reflected pulses are detected.

The technique of electrical impedance computed tomography does not employ high-frequency ultrasonic waves or penetrating radiation such as X-rays, but instead uses weak electrical currents to map out the electrical properties of the material, such as human tissue. While this technique has the advantage of reduced health hazard, it suffers from the same disadvantage as the ultrasonic tomographic technique in that the detectors must be placed in good contact with the skin of the patient. Thus, it is essential to establish good electrical contact between the skin of the patient and the electrode detector system, otherwise it is impossible to detect with any degree of accuracy the weak electrical currents which are used. In this event, the resulting reconstructed images have very poor resolution.

A recent development in the tomography area is nuclear magnetic resonance (nmr) tomography, also known as zeugmatography. This technique makes use of the fact that nuclei, typically individual protons or hydrogen nuclei, have a small nuclear moment and an associated spin angular momentum. The combined effect of the magnetic moment and spin gives rise to precession on the nuclei about the direction of an applied magnetic field similar to the way in which a spinning top precesses when perturbed from the upright position. In the nmr technique, a magnetic gradient is applied to the sample, and the nuclei tend to polarize or align themselves along the direction of the magnetic field giving rise to a bulk magnetization of the sample. A perturbing pulse or pulses is applied to the sample to perturb the magnetization through, for example 90°, and repolarization occurs according to the spin-lattice relaxation time which is characteristic of the electronic environment of the nuclei. The frequency of precession, known as the Larmor frequency, is typically in the range of 10 to 100 MHz, and this requires the application of relatively high strength magnetic fields arranging from about 0.235 to 2.35 Teslar (corresponding to about 2.35 to 23.5 kilogauss). By applying the magnetic field gradient through a cross-section of the body, it is possible to obtain the spin-lattice relaxation times across the cross-section and to use these to create a picture reflective of the variation of proton density over the cross-section. Although the Larmor technique appears to have good potential in the diagostic field, it is not yet known whether ill effects arise as a result of being subjected to the relatively high magnetic field strengths involved. A major disadvantage of the technique is that presently available devices are incapable of penetrating more than about one or two inches into the tissue.

A recent approach which has been taken in the non-destructive testing area is to investigate the dielectric constant and conductivity properties of materials. In a recent article appearing in "Electronics International", published Jan. 23, 1980, an instrument referred to as a "mammo-scanner" is described, which allegedly aids in the early detection of breast cancer. The mammo-scanner appears to be the subject of U.S. Pat. No. 4,144,877 to Frei et al, issued Mar. 20, 1979, and operates by measuring the variations of dielectric constant and conductivity of the breast tissue. This technique is essentially the same as electrical impedance computer tomography discussed earlier, in that the detector must be contacted with the tissue in order to obtain useful output data. The device shown in the Frei patent is constructed in the form of a hand glove which permits the examiner to conduct a palpation procedure over the entire surface of the breast tissue. The variations in dielectric constant are displayed, for example, on a gray scale, and any large fluctuations over the surface of the breast tissue indicate that further investigation for possible cancerous tissue may be required.

U.S. patent application Ser. No. 28,452, assigned to Georgetown University, the disclosure of which is specifically incorporated herein by reference, relates to identification of materials using their dielectric constant and conductivity properties. Identification is achieved by bringing the entire sample to be identified into the influence of a field and measuring the dielectric and conductance properties of the material as a whole over a range of pre-selected frequencies. It is possible to directly identify the materials under investigation using this technique, typically explosives and drugs, but some difficulties arise when these materials form only a part of a larger object possibly composed of many component materials which is brought into the influence of the field. This situation arises, for example, when a small volume of an explosive material or a drug is concealed in a large package such as a mail parcel or piece of hand luggage. The situation can also arise in the medical field where a small mass of cancerous tissue is present in a large area of healthy tissue. In these instances, it is difficult to accurately identify the concealed small volume sample using the technique of the above United States patent application, which means that the technique is limited essentially to an overall identification of the entire volume of material brought within the influence of the field.

U.S. patent application Ser. No. 871,099, now U.S. Pat. No. 4,263,551, assigned to Georgetown University, the disclosure of which is specifically incorporated herein by reference, relates to identification of conductive materials by measuring the true resistive component of the impedance change which occurs when the material is brought within the influence of a magnetic field generated by a stable coil system. When the true resistive component is divided by the respective applied frequency, a value is obtained which varies with frequency and peaks at a single peak frequency. At the peak frequency, the value of the true resistive component divided by the frequency is proportional to the resistivity of the material divided by its cross-sectional area. Again, it is difficult to accurately identify a concealed small volume sample of conductive material using this technique.

SUMMARY OF THE INVENTION

According to the present invention, there is provided a contactless, non-destructive, substantially hazard-free and relatively low cost technique for generating pictorial images of discrete portions or volume elements of a material under investigation, which technique does not suffer from the problems associated with the various prior techniques described above. In the present invention, the material under investigation is introduced into the influence of a relatively low strength electromagnetic field generated, for example, by spaced apart capacitive plates or by an electrically stable coil system and, while maintaining the material out of physical contact with the plates or coil system, the magnetic and/or electric permeability and/or conductance values of the material over a range of pre-selected frequencies are measured for individual volume elements, typically adjacent or adjoining volume elements, of the material defined by intersecting field lines and/or planes of the material. These magnetic, electric and conductance values are obtained by measuring the output signal obtained for each applied frequency and resolving these signals into respective resolved reactive and non-reactive component values, each reflective of the respective magnetic, electric and conductance values of the particular volume element of material in the field at the respective applied frequency. By varying the positional orientation of the material with respect to the applied field, for example by moving the material and the plates (or coil system) relative to each other, or by moving both the material and the plates, or by keeping the material and the plates stationary and electronically multiplexing a series of smaller plates to vary the directional orientation of the field, magnetic and/or electric permeability and/or conductance values are obtained from the respective resolved reactive and non-reactive component values for different volume elements of the material. From these values, a pictorial image of the respective volume elements of the material is generated which is reflective of the magnetic and/or electric and/or conductance properties of the volume element.

From the above, it will be appreciated that the invention of the present application enjoys numerous advantages over the prior techniques described earlier. In particular, the present technique is contactless, that is, it is not necessary to establish and maintain any direct physical contact between the plates or coils and the object or material under investigation. This is particularly advantageous in the medical application of the present technique where the need to carefully position leads, electrodes or probes on the patient's skin is eliminated.

Another advantage, already noted earlier, resides in the fact that the present technique utilizes low-strength electromagnetic fields which not only are free from serious health hazard problems, but also are non-destructive of the sample or material under investigation. This, again, is of prime importance in the medical application of the present technique.

A further advantage of the present technique is that the data obtained with respect to each volume element of the material has a high information content with respect to parameters of the material. Thus, the data obtained contains useful information measured over plural frequencies with respect to numerous parameters which are independently significant from a material identification and image generation standpoint. When, for example, capacitor plates are employed to sense the material, the data obtained over plural frequencies contains electrical information with respect to each selected volume element which is used to generate an image reflective of the dielectric constant and conductance parameters of the selected volume elements of the material. This is to be contrasted with X-ray tomography which is essentially a single parameter (density) measurement, which generates images reflective only of the density of the slice of interest.

A further advantage of the technique of the present invention is that it employs a rigorous interative computational process, as opposed to a less rigorous empirical process, to correct for irregularities in the shape of the field lines passing through the material within the influence of the field. In essence, this iterative process demands that the shape of the field lines in the material comply, mathematically, with the unique field line shape computed for that material by solving the appropriate Maxwell equations. This iterative correction process results in a rigorous and accurate picture which would not be obtained if empirical correction techniques were used.

It can be appreciated, therefore, that it is possible according to the invention to, for example, locate, isolate and display as an actual picture in grey scale or in color a small area of cancerous tissue within a larger region of healthy tissue without subjecting the tissue to hazardous penetrating radiation, for example X-rays, or to possibly harmful high-strength electromagnetic fields, such as those employed in nmr tomography, and further without having to establish and maintain any direct physical contact between the tissue and the field generator (coils and/or capacitive plates) or the detector (leads, electrodes or probes) of the system.

BRIEF DESCRIPTION OF THE DRAWINGS

The invention of this application will be further understood from the following description which is made with reference to the accompanying drawings, in which.

DETAILED DESCRIPTION OF THE INVENTION

To further assist in understanding the present invention, the following discussion is presented to summarize the theoretical basis underlying the invention. For convenience in this discussion reference will be made to capacitances and to the use of a capacitive field, but it will be appreciated that the invention is equally applicable to other types of electromagentic field systems, for example a magnetic field generated by an electrically stable coil system.

Figure 6:
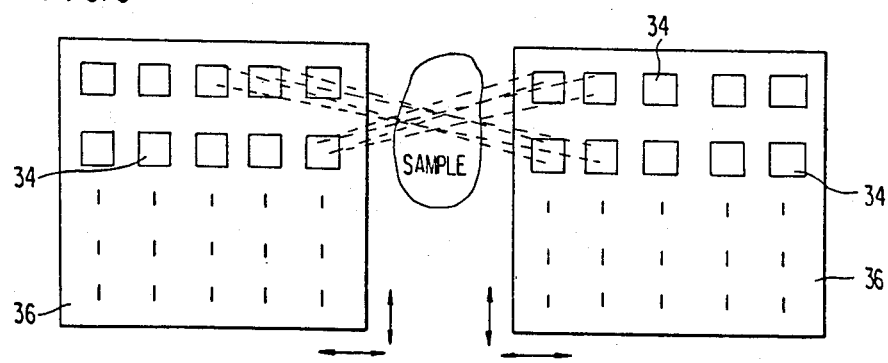
FIG. 6 shows schematically one arrangement of plural multiplexible capacitive plates.

The object to be investigated and the capacitive plates are moved with respect to each other and out of physical contact with each other so that different volume elements of the object usually adjacent to each other and defined by intersecting field lines and/or planes of the object are subjected to the influence of the electric field over a range of applied pre-selected frequencies. Output signal data reflective of the dielectric constant and conductance properties of these portions is collected and subsequently used for generation of pictorial images reflective of the dielectric constant and conductance properties of the respective volume elements. A sample mover 33 (FIG. 1) can be used for moving the sample relative to the plates. Alternatively, the capacitive plates can be maintained stationary and arranged in such a way as to be composed of a series of smaller capacitive plates 34 (FIG. 6) mounted in a guard ring 36 and electronically multiplexible with respect to each other via a multiplexer unit 35 (FIG. 1) in order to vary the directional orientation of the electric field through the object. FIGS. 2A and 2B show, schematically, movement of an object 2 within a field generated between capacitor plates 4. By subtracting capacitance values b from a, value c is obtained for the slice S. Then by moving the object 2 with respect to the field, capacitance values are obtained for selected cross-sectional volume elements defined by intersecting field lines and/or planes of the object.

Figure 2A:
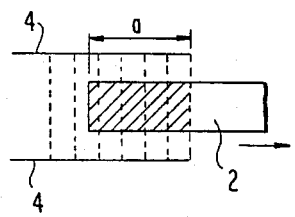
FIGS. 2A, 2B, 2C, 3A and 3B are presented to assist in understanding a discussion of underlying theory set forth in the detailed description of the invention.
Figure 2B:
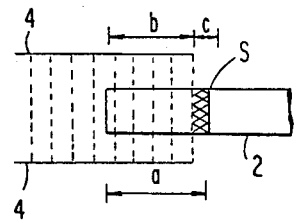
Figure 2C:
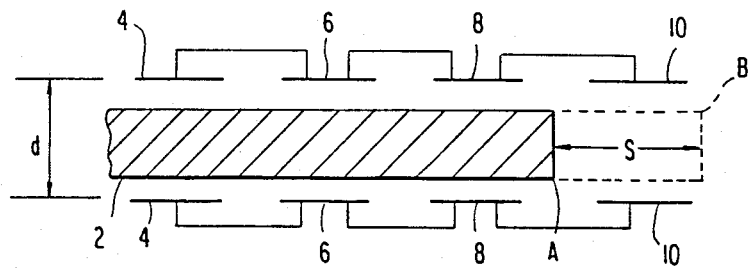

An equivalent circuit model of object 2 inserted at two different positions A and B between capacitive plates 4, 6, 8, 10 is shown in FIG. 2C. In position A, the resulting capacitance is the sum of several parallel capacitances and is given by:

$$\tilde{C}_a = \sum_{i=1}^{N} \tilde{C}_i \qquad (\text{Eq. 1})$$

In position B, the capacitance is given by:

$$\tilde{C}_B = \sum_{i=1}^{N+1} \tilde{C}_i \qquad (\text{Eq. 2})$$

In Equations 1 and 2, the capacitances expressed can be treated as complex quantities having real and imaginary parts, the real part being related to the dielectric constant and the imaginary part to the losses or tric constant and the imaginary part to the losses or conductance of the material. The difference in capacitance for the two different insertions of the material between the capacitive plates leads to a capacitance for slice S of the material which has the capacitance value:

$$-\tilde{C}_A + \tilde{C}_B = \Delta \tilde{C}_{N+1} = \tilde{\epsilon}_{avg} \frac{A}{d} \quad (\text{Eq. 3})$$

where A is the area of the plates, d is the distance between the plates and $E_{avg}$ is the average complex dielectric constant measured over the whole thickness d.

Figure 3A:
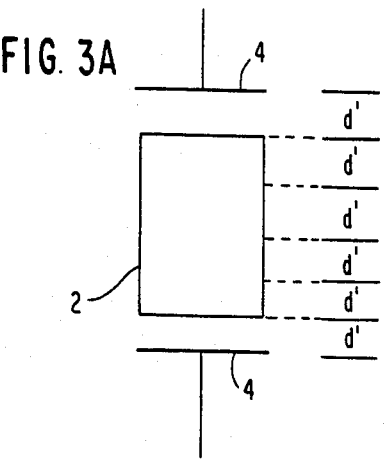
Figure 3B:
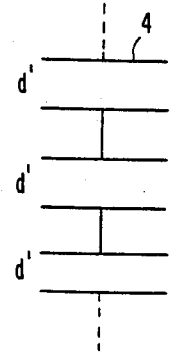

By examining the capacitance of slice S, it will be noted that it may be considered as a sum of capacitances of elements in series such as that shown in FIGS. 3A and 3B. This sum is given by the inverse sum of the capacitances and is equal to the inverse of the total capacitance. This may be written as follows:

$$\frac{1}{\Delta \tilde{C}_{N+1}} = \sum_j \frac{dj}{\tilde{\epsilon}_{n+1,j}} \frac{1}{A} \quad (\text{Eq. 4})$$

From the above, it can be seen that the capacitance measurement at each frequency for each slice of material is the inverse of the total capacitance for the slice which in turn is related to the inverse sum of the capacitances of the elements of the slice.

Figure 4:
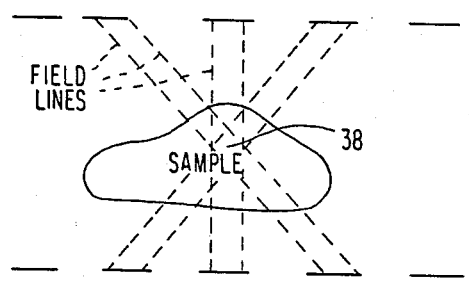
FIGS. 4 and 5 illustrate schematically different configurations of multiplexable capacitive plates.
Figure 5:
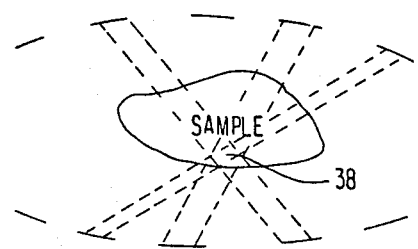

By moving the sample and the capacitive plates with respect to each other to generate various individual intersecting field strips in the object between the capacitive plates, either by relative movement of the object and the capacitive plates or by multiplexing a series of smaller capacitive plates, it is possible to obtain a series of measurements of the quantities $\Delta C_n$ which can be equal in number to the number of unknown capacitance values, real and imaginary, contained within one or more volume elements 38 of the object as defined by intersecting field lines and/or planes of the object. This is shown, for example, in FIG. 4. Then by using conventional computer tomographic techniques (mentioned above as "reconstruction from projections" in "BACK-GROUND OF THE INVENTION"), it is possible to reconstruct, by computer algorithm, a pictorial image of each of the volume elements from these real and imaginary capacitance values, which image is reflective of the dielectric constant and conductance values (i.e. the complex dielectric constant values, $\epsilon i,j$) for the respective volume elements in the object.

The calculations illustrated in Equations 1 through 4 are intended to apply strictly to a situation where fringing electronic fields are eliminated. This may be achieved to a large extent with the use of electric guard rings 36 (FIG. 6), but it is possible with the present technique to apply additional corrections to the fields to further eliminate these fringe field effects. For example, a rigorous iterative computer process can be used which assumes a value for the conductance and dielectric constant values in each of the volume elements and requires that the sum of these values for the series of measurements must in each case equal, to within a prespecified error limit, the value of $\Delta C_n$ as physically measured. The iteration procedure continues until the sum of these values equals, to within the pre-specified error limit, the actual physically measured values. A further rigorous iterative correction technique which can be applied is to demand that the field or potentials obtained everywhere within the volume enclosed within the capacitive plates are rigorous solutions of the appropriate Maxwell's equations. Techniques for solving Maxwell's equations by mathematical methods are known as Finite Difference techniques, and these allow for a rigorous solution that can be incorporated within the iterations required in the tomographic calculation. It is to be noted that the Finite Difference technique permits a rigorous solution for dielectric constant measurements whereas, for ultrasound and X-ray tomographic techniques, similar corrections (sometimes referred to as "filter functions") are relatively rough approximations which must be empirically modified for every object measured by the ultrasound or X-ray tomographic technique.

Figure 1:
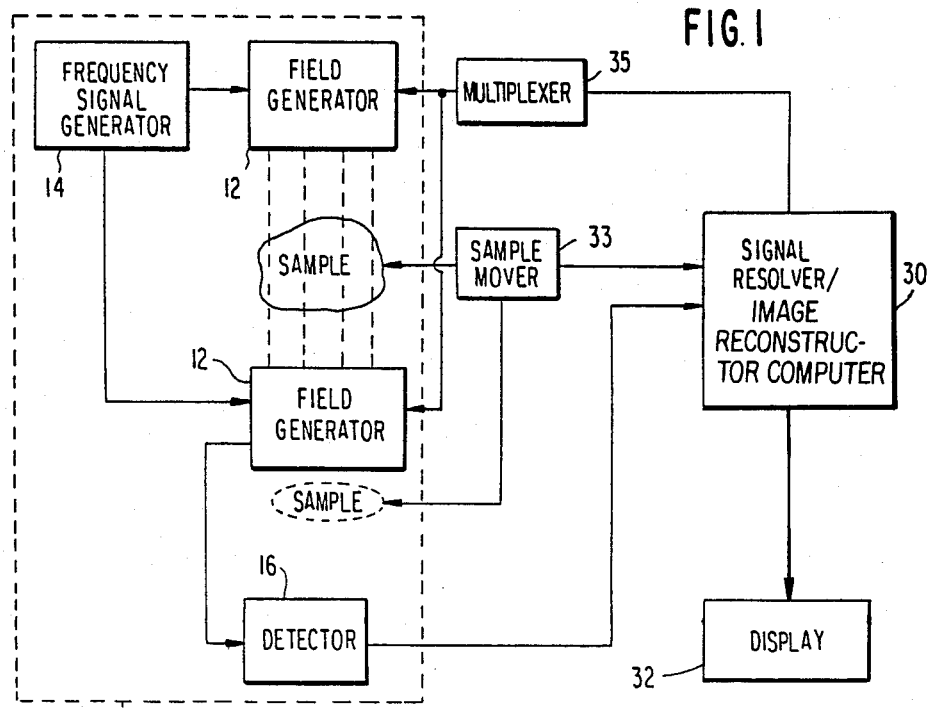
FIG. 1 is a schematic block diagram of the apparatus of the present invention showing alternative locations of the sample to be investigated.

Referring now to the apparatus of the invention, this is shown schematically in block diagram form in FIG. 1. The apparatus comprises an electromagnetic field generating means 12, typically spaced-apart capacitive plates, an electrically stable coil system or, possibly, spaced-apart probes, for generating a relatively low-strength electromagnetic field. The electromagnetic field generating means is connected to a frequency generating means 14 and to a detector 16. The term "relatively low-strength" as used herein means that the field has a strength sufficient to produce a measurable response but not sufficient to cause any adverse health effects when human or animal tissue is subjected to the influence of the field. Generally, the strength of the capacitive electric field is within the range of 20 to 700 volts per meter of plate surface area, more typically 90 to 600 volts per meter, for example 400 to 600 volts per meter. When an electrically stable magnetic coil system is used as the electromagnetic field generating means 12, again the applied magnetic field is a relatively low-strength field which is free from any possible health hazard.

The expression "electrically stable coil system" as used herein means the stability is held to at least one part in ten thousand of rated values, preferably one part in one hundred thousand, with the coil as free as possible from all extraneous effects. Spacing between adjacent turns of the coil, temperature stability of the wire, and absence of temperature variations are key factors in maintaining this stability. Generally, the magnetic field strength ranges from about 100 milligauss to 1 gauss, more typically 500 milligauss to about 0.5 gauss. From this, it will be noted that the magnetic field strengths employed in this invention are substantially lower than the magnetic field strengths used in nmr tomography where the field strengths range typically from about 2 kilogauss to 25 kilogauss.

The electromagnetic field generating means 12 produces an output signal which is reflective of the magnetic and/or electric permeability and/or conductance properties of the volume element of the object brought within the influence of the electromagnetic field. During this measurement, the material is maintained out of physical contact with the electromagnetic field generating means 12, as shown schematically in FIGS. 1 through 6.

Figure 8:
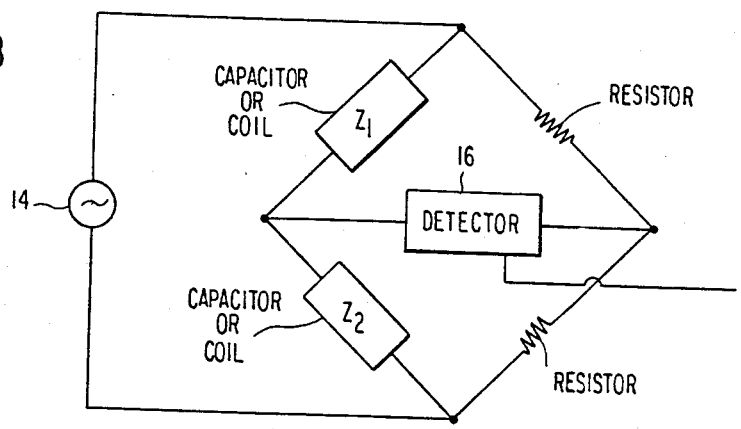
FIGS. 8 through 10 illustrate circuits for the generation of an electromagnetic field and the detection of an output signal, forming part of the overall scheme of FIG. 1.
Figure 9:
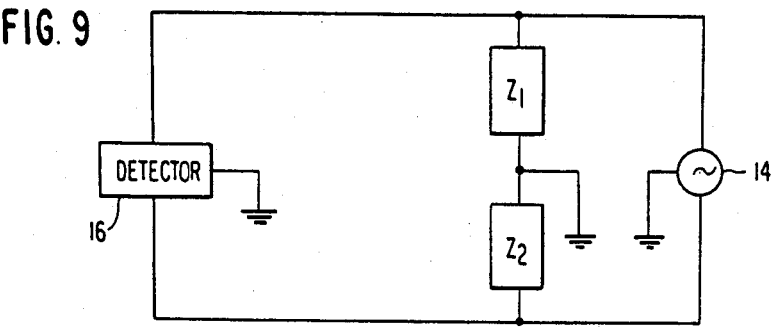
Figure 10:
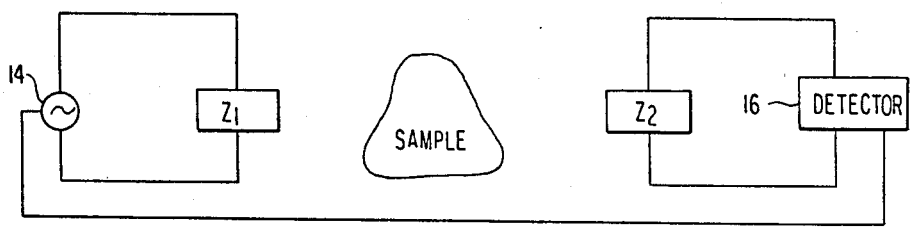

When the dielectric constant and conductance properties of the sample object are being measured, the electromagnetic field generating means 12 includes at least two spaced apart capacitive plates 4, 6, 8, 10 (FIG. 2c) which are also shown schematically by $Z_1$ and $Z_2$ in the circuit diagrams of FIGS. 8 through 10 ($Z_1$ and $Z_2$ alternately can be coils if magnetic fields are being used). FIGS. 8 through 10 show different possible circuit arrangements for the portion E enclosed by broken line in the block diagram of FIG. 1. FIG. 8, for example, shows a bridge circuit in which the capacitances $Z_1$ and $Z_2$ are contained in a balanceable bridge circuit in which the detector 16 is nulled when the bridge is balanced. FIGS. 9 and 10 show alternative possible circuit arrangements for the elements $Z_1$ and $Z_2$ connected to detector 16 and frequency generating means 14. These circuitry aspects of the present invention are similar to those described in the abovementioned U.S. patent applications Ser. Nos. 28,452 and 871,099, the disclosure of which are incorporated herein by reference.

The capacitive plates which comprise the field generating means 12 are driven by a frequency signal generating means 14, typically a sine wave generator, which creates an alternating electric field between the capacitive plates. As indicated above, discrete volume elements of the sample are subjected to the alternating electric field at various plural pre-selected frequencies which are generally in the lower radio frequency range. The frequencies employed usually range from 10 hertz to 200 kilohertz, more usually 20 hertz to 150 kilohertz, for example 20 kilohertz to 100 kilohertz. There are no known health hazards to human or animal tissue when subjected to field frequencies in these ranges.

Figure 7A:
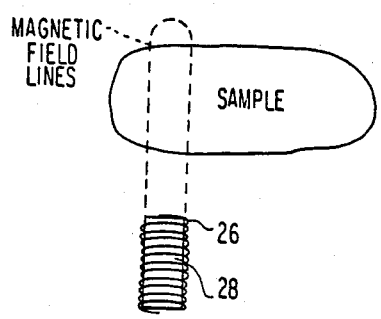
FIGS. 7A, 7B, 7C and 7D show schematically the use of magnetic fields in relation to a sample.
Figure 7B:
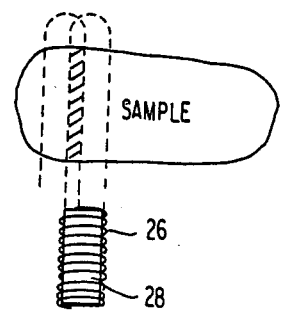
Figure 7C:
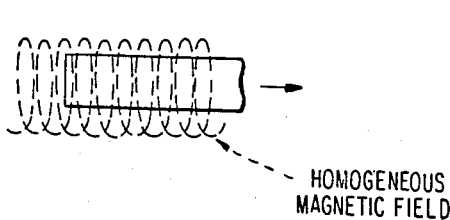
Figure 7D:
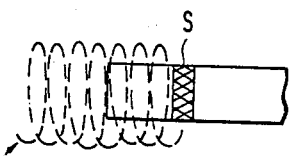

FIGS. 7A, 7B, 7C and 7D illustrate the instance where the field generating means is a coil system. In FIGS. 7A and 7B, a coil 26 is shown having a core 28 which causes the generation of a non-homogeneous magnetic field extending generally in the direction of the longitudinal axis of the core 28. By moving the sample and the coil with respect to each other, it is possible to obtain output signal data in respect of particular volume elements of the sample subjected to the magnetic field and to resolve this output signal data into respective resistive and inductive component values which are reflective of the magnetic properties of the material. It is preferred to obtain the true resistive component of the impedance change in the coil system at each of the applied pre-selected frequencies. This "true" resistive component is obtained by referencing the output signal of the coil system generally to within about one degree (preferably, half a degree) of the phase of the signal applied to the coil system for each of the applied pre-selected frequencies. The coil system generates a low-strength magnetic field as discussed above, and no health hazards are known to exist when human or animal tissue is brought within the influence of these magnetic fields. FIGS. 7C and 7D illustrate the use of a homogenous magnetic field to obtain information concerning a particular volume element S. As with capacitive value, the magnetic properties of the selected volume element S are obtained by computing the difference in these properties for different degrees of insertion of the sample in the magnetic field.

The output signals generated by the electromagnetic field generating means 12 (FIG. 1) are detected by a detector 16 and resolved into the respective components in an output signal resolving means 30. Usually, the detector is a phase sensitive detector, although any other suitable detecting device may be employed. More typically, the signal resolving means 30 serves both to detect the output signals and to resolve them into the respective reactive and non-reactive component values prior to tomographic reconstruction and display as a pictorial image. Thus, when the field generating means is a capacitive system, the output signal is resolved by the signal resolving means 30 into capacitive and conductive component values and at least one of these components is used by the signal resolver 30 (e.g. a digital computer) to generate image data reflective of the dielectric constant and conductance properties of the material under investigation. The image data is then displayed as a pictoral image on image generating means 32, typically a cathode ray tube display.

Image reconstruction in the present invention can be achieved using conventional reconstruction techniques such as, for example, the filtered back-projection method described by Bracewell et al, "Inversion of Fan-Beam Scans in Radio Astronomy", Astrophysics J. 150:427–434. However, it is emphasized that the present invention is not limited to the use of this particular reconstruction technique, and other available methods can be employed if desired.

The pictorial image generated by the generating means 32 may be made up of a series of darker and lighter contrasting zones, for example a gray scale or a spectrum of selected colors. The intensity and/or variation in appearance in these zones is proportional to the value of the dielectric constant and/or conductance values of the volume element of the body represented by the image. It is also possible for example in the medical diagnostic area, to designate certain colors as representing normal or abnormal tissue constitution. In this way, it is possible to quickly determine from the color display whether suspicious tissue formation is present, and where this tissue is located in relation to the surrounding mass of healthy tissue.

Figure 11A:
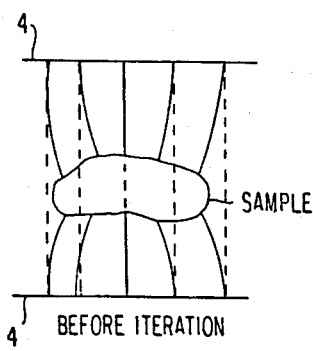
FIGS. 11A and 11B illustrate schematically the effect of iteration on field lines in the region of the sample.
Figure 11B:
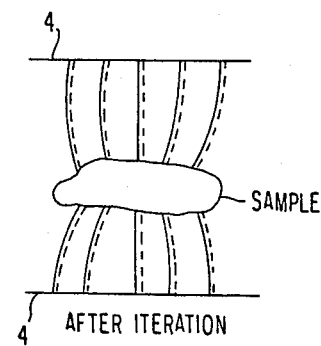

As described earlier, the present technique includes a rigorous interative correction technique to bring the field lines in the sample into compliance with the solutions to the appropriate Maxwell's equations. The effect of this iteration is shown schematically in FIGS. 11A and 11B, where FIG. 11A shows the field shape prior to iteration and FIG. 11B shows the field shape after iteration. The iteration procedure produces more accurate and reproducible image data which in turn results in the generation of accurate and reproducible pictorial images.

What is claimed is:

1. Apparatus for generating an image of a material using at least one of its magnetic, electric permeability and conductance properties under substantially hazard-free field conditions and without establishing physical contact with the material, said apparatus comprising:

(a) electromagnetic field generating means for generating a relatively low-strength substantially hazard-free electromagnetic field and for producing an output signal when the material to be investigated is brought within the influence of said electromagnetic field and out of physical contact with said electromagnetic field generating means, said output signal having a value which is reflective of said at least one of the magnetic, electric permeability and conductance properties of at least one volume element of said material, said at least one volume element being defined by at least one of intersecting field lines of said electromagnetic field and intersecting planes of said material;

(b) frequency generating means connected to said electromagnetic field generating means for producing a frequency signal comprising a plurality of pre-selected frequencies, said frequency signal being applied to said electromagnetic field generating means for generating said electromagnetic field;

(c) output signal resolving means connected to said electromagnetic field generating means for resolving said output signal into separate resolved component values including a resolved reactive component value and a resolved non-reactive component value to said at least one volume element of said material for each of said pre-selected frequencies; and (d) image generating means connected to said output signal resolving means for generating a pictorial image of said material from at least one of said resolved component values for at least one volume element, said pictorial image being reflective of said at least one of the magnetic, electric permeability and conductance properties of said at least one volume element.

2. Apparatus according to claim 1 and further including moving means located in the vicinity of said electromagnetic field generating means for causing relative movement of said material and said electromagentic field, whereby said at least one volume element of said material is brought within the influence of said electromagnetic field.

3. Apparatus according to claim 2 wherein said moving means moves said material to be investigated while said electromagnetic field generating means is maintained stationary.

4. Apparatus according to claim 1, wherein said electromagnetic field generating means comprises a coil system to which a signal having a phase is applied, and wherein the output signal of the electromagnetic field generating means is referenced to within about one degree of the phase of the signal applied.

5. Apparatus for generating an image of a material using its dielectric constant and conductance properties under substantially hazard-free electric field conditions and without establishing physical contact with the material, said apparatus comprising:

(a) capacitive means for generating a relatively low-strength substantially hazard-free electric field and for producing an output signal when the material to be investigated is brought within the influence of said electric field, said capacitive means including at least one capacitive element, said material being positionable within the influence of said electric field while out of physical contact with said capacitive element, said output signal having a value which is reflective of the dielectric constant and conductance properties of at least one volume element of said material, said at least one volume element being defined by at least one of intersecting field lines of said electric field and intersecting planes of said material;

(b) frequency generating means for producing a frequency signal comprising a plurality of preselected frequencies, said frequency signal being applied to said capacitive means for generating said electric field;

(c) output signal resolving means connected to said capacitive means for resolving said output signal into separate resolved component values, including a resolved capacitive component value and a resolved conductive component value for said at least one volume element of said material for each of said pre-selected frequencies; and (d) image generating means connected to said output signal resolving means for generating a pictorial image of said material from at least one of said resolved component values for said at least one cross-sectional volume element, said pictorial image being reflective of at least one of the dielectric constant and conductance properties of said at least one volume element of said material.

6. Apparatus according to claim 5 wherein said at least one capacitive element includes at least two spaced apart capacitive plates having multiplexing means for adjusting the relative directional orientation of said electric field between and in the vicinity of said plates.

7. Apparatus according to claim 6 wherein said multiplexing means includes a plurality of capacitive units surrounded by at least one guard ring.

8. Apparatus for generating an image of material using its magnetic and conductance properties under substantially hazard-free magnetic field conditions and without establishing physical contact with the material, said apparatus comprising:

(a) magnetic field generating means for generating a relatively low-strength substantially hazard-free magnetic field and for producing an output signal when a material to be investigated is brought within the influence of said magnetic field, said magnetic field generating means including at least one electrically stable coil system, said material being positionable within the influence of said magnetic field while out of physical contact with said coil system, said output signal having a value which is reflective of the magnetic and conductance properties of at least one volume element of said material, said at least one volume element being defined by at least one of intersecting magnetic field lines of said magnetic field and intersecting planes of said material;

(b) frequency generating means connected to said magnetic field generating means for producing a frequency signal comprising a plurality of preselected frequencies, said frequency signal being applied to said magnetic field generating means for generating said magnetic field;

(c) output signal resolving means connected to said magnetic field generating means for resolving said output signal into separate resolved component values including a resolved true resistive component value and a resolved conductive value for said at least one volume element of said material for each of said pre-selected frequencies; and (d) image generating means connected to said output signal resolving means for generating a pictorial image of said material from at least one of said resolved component values for said at least one volume element, said pictorial image being reflective of the magnetic and conductive properties of said at least one volume element of said material.

9. Apparatus according to claim 8 wherein said at least one electrically stable coil system includes at least one coil which generates a magnetic field along the longitudinal axis of said coil.

10. Apparatus according to claim 8, wherein a signal having a phase is applied to said electrically stable coil system, and the output signal is referenced to within about one degree of the signal applied.

11. Apparatus for generating an image of a human or animal body or part thereof using the dielectric constant and conductance properties of the body under substantially hazard-free electric field conditions and without establishing physical contact with the body, said apparatus comprising:

(a) capacitive means for generating a relatively low-strength substantially hazard-free electric field and for producing an output signal when said human or animal body or part thereof to be investigated is brought within the influence of said electric field, said capacitive means including at least one capacitive element having at least two spaced apart capacitive plates, said body and said capacitive means being movable relative to each other to vary the influence of said electric field while out of physical contact with said at least two spaced apart capacitive plates, said output signal having a value which is reflective of the dielectric constants and conductance properties of at least one volume element of said body, said at least one volume element being defined by at least one of intersecting field lines of said electric field and intersecting planes of said body;

(b) frequency generating means for producing a frequency signal comprising a plurality of pre-selected frequencies, said frequency signal being applied to said capacitive means for generating said electric field;

(c) output signal resolving means connected to said capacitive means for resolving said output signal into separate resolved component values including a resolved capacitive component value and a resolved conductive component value for said at least one volume element of said body for each of said pre-selected frequencies; and (d) image generating means connected to said output signal resolving means for generating a pictorial image of said body from at least one of said resolved component values for said at least one volume element, said pictorial image being reflective of the dielectric constant and conductance properties of said at least one volume element of said material.

12. Method for generating an image of a material using at least one of its magnetic, electric permeability and conductance properties under substantially hazard-free field conditions and without establishing physical contact with the material, said method comprising the steps of:

(a) generating a relatively low-strength substantially hazard-free electromagnetic field so as to produce an output signal when a material to be investigated is brought within the influence of said electromagnetic field, said output signal having a value which is reflective of said at least one of the magnetic, electric permeability and conductance properties of at least one volume element of said material, said at least one volume element being defined by at least one of field lines of said electromagnetic field and intersecting planes of said material;

(b) establishing a reference value of said output signal in the absence of said material within the influence of said electromagnetic field, said output signal being measured with respect to a plurality of frequencies applied to said electromagnetic field generating means, said frequencies being pre-selected so that said output signal has a value which is reflective of said at least one of said magnetic, electric permeability and conductance properties when said material is brought within the influence of said electromagnetic field;

(c) introducing material to be investigated into the influence of said electromagnetic field at said plural pre-selected frequencies to produce an output signal having a value which is reflective of said at least one of the magnetic, electric permeability and conductance properties of said at least one volume element of said material;

(d) resolving said output signal into separate resolved component values including a resolved reactive component value and a resolved non-reactive component value for said at least one volume element of said material for each of said pre-selected frequencies; and (e) generating a pictorial image of said material from at least one of said resolved reactive and non-reactive component values for at least said at least one volume element, said pictorial image being reflective of said at least one of the magnetic, electric permeability and conductance properties of said at least one volume element of said material.

13. Method according to claim 12 and further including the step of correcting for irregularities in the electromagnetic field caused by the presence of the material within the influence of the electromagnetic field by iterating said resolved reactive and non-reactive component values for said at least one volume element at each of said pre-selected frequencies, to thereby enhance the pictorial image generated by said image generating means.

14. Method according to claim 12 wherein said material is moved relative to the influence of said electromagnetic field while out of physical contact with said electromagnetic field.

15. Method according to claim 12 wherein said material is maintained stationary and said electromagnetic field is moved relative to said material with said material being within the influence of said electromagnetic field.

16. Method according to claim 12, wherein said electromagnetic field is produced as a result of application of a signal having a phase, and the output signal is referenced to within about one degree of the phase of the signal applied.

17. Method for generating an image of a human or animal body or part thereof using its dielectric constant and conductance properties, under substantially hazard-free capacitive electric field conditions and without establishing any physical contact with the body, said method comprising the steps of:

(a) providing a capacitive means for generating a relatively low-strength substantially hazard-free electric field so as to produce an output signal when said human or animal body or part thereof is brought within the influence of said electric field, said capacitive means including at least one capacitive element having at least two spaced apart capacitive plates, said body and said capacitive means being movable relative to one another, said body being within the influence of said electric field and out of physical contact with said at least two spaced apart capacitive plates, said output signal having a value which is reflective of the dielectric constant and conductance properties of at least one volume element of said body, said at least one volume element being defined by at least one of intersecting field lines of said electric field and intersecting planes of said body;

(b) establishing a reference value of an output signal of said capacitive means in the absence of said body within the influence of said electric field, said output signal being measured with reference to a plurality of frequencies applied to said capacitive means, said frequencies being pre-selected so that said output signal has a value which is reflective of the dielectric constant and conductance properties when said at least one volume element of said body is brought within the influence of said electric field;

(c) introducing said human or animal body or part thereof to be investigated into the influence of said electric field at said plurality of pre-selected frequencies to produce an output signal having a value which is reflective of the dielectric constant and conductance properties of said at least one volume element of said body;

(d) resolving said output signal into separate resolved component values including a resolved capacitive component value and a resolved conductive component value for said at least one volume element of said body for each of said pre-selected frequencies; and (e) generating a pictorial image of said body from at least one of said resolved capacitive and conductive component values for said at least one volume element, said pictorial image including regions of contrasting lighter and darker zones and being reflective of the dielectric constant and conductance properties of said at least one volume element of said body.

* * * * *